United States Patent
Del Gaudio et al.

(10) Patent No.: US 9,884,299 B2
(45) Date of Patent: Feb. 6, 2018

(54) PROCESS FOR THE PREPARATION OF WATER-IN-OIL AND OIL-IN-WATER NANOEMULSIONS

(71) Applicants: Lucilla Del Gaudio, San Donato Milanese (IT); Thomas Paul Lockhart, Lodi (IT); Alessandra Belloni, Cerro al Lambro (IT); Rossella Bortolo, Novara (IT); Roberto Tassinari, Novara (IT)

(72) Inventors: Lucilla Del Gaudio, San Donato Milanese (IT); Thomas Paul Lockhart, Lodi (IT); Alessandra Belloni, Cerro al Lambro (IT); Rossella Bortolo, Novara (IT); Roberto Tassinari, Novara (IT)

(73) Assignees: ENI S.p.A., Rome (IT); POLIMERI EUROPA S.p.A., San Donato Milanese (IT)

( * ) Notice: Subject to any disclaimer, the term of this patent is extended or adjusted under 35 U.S.C. 154(b) by 448 days.

(21) Appl. No.: 13/845,515

(22) Filed: Mar. 18, 2013

(65) Prior Publication Data

US 2013/0209527 A1    Aug. 15, 2013

Related U.S. Application Data

(62) Division of application No. 12/294,552, filed as application No. PCT/EP2007/002863 on Mar. 28, 2007, now Pat. No. 8,431,620.

(30) Foreign Application Priority Data

Mar. 31, 2006   (IT) .............................. MI2006A0618

(51) Int. Cl.
| | |
|---|---|
| *B01F 3/08* | (2006.01) |
| *A61K 9/107* | (2006.01) |
| *B01F 17/00* | (2006.01) |
| *C09K 8/524* | (2006.01) |
| *C09K 8/528* | (2006.01) |
| *C09K 8/54* | (2006.01) |
| *C10L 1/32* | (2006.01) |

(52) U.S. Cl.
CPC .......... *B01F 3/0811* (2013.01); *A61K 9/1075* (2013.01); *B01F 17/0085* (2013.01); *C09K 8/524* (2013.01); *C09K 8/528* (2013.01); *C09K 8/54* (2013.01); *C10L 1/328* (2013.01); *B01F 2003/083* (2013.01); *B01F 2003/0823* (2013.01)

(58) Field of Classification Search
USPC ....................................................... 516/21
See application file for complete search history.

(56) References Cited

U.S. PATENT DOCUMENTS

| | | | |
|---|---|---|---|
| 5,658,575 A * | 8/1997 | Ribier et al. .................. 424/401 |
| 2002/0035182 A1* | 3/2002 | L'Alloret et al. ............ 524/315 |
| 2002/0155084 A1 | 10/2002 | Roessler et al. | |
| 2006/0030655 A1 | 2/2006 | L'Alloret et al. | |

FOREIGN PATENT DOCUMENTS

| | | |
|---|---|---|
| EP | 1 172 077 | 1/2002 |
| EP | 1 984 477 B1 | 10/2012 |

* cited by examiner

*Primary Examiner* — Johann R Richter
*Assistant Examiner* — Danielle D Sullivan
(74) *Attorney, Agent, or Firm* — Oblon, McClelland, Maier & Neustadt, L.L.P.

(57) ABSTRACT

Process for the preparation of a water-in-oil or oil-in-water nanoemulsion wherein the dispersed phase is distributed in the dispersing phase in the form of droplets having a diameter ranging from 1 to 500 nm, comprising:
1) the preparation of a homogeneous water/oil blend (I) characterized by an interface tension lower than 1 mN/m, comprising water in an amount of 30 to 70% by weight, at least two surface-active agents having a different HLB, selected from non-ionic, anionic, polymeric surface-active agents, said surface-active agents being present in such a quantity as to make the blend homogeneous;
2) the dilution of the blend (I) in a dispersing phase consisting of oil or water with the addition of a surface-active agent, selected from non-ionic, anionic, polymeric surface-active agents, the quantity of the dispersing phase and surface-active agent being such as to obtain a nanoemulsion having a HLB different from that of the blend (I).

17 Claims, No Drawings

PROCESS FOR THE PREPARATION OF WATER-IN-OIL AND OIL-IN-WATER NANOEMULSIONS

This application is a divisional of U.S. application Ser. No. 12/294,552, filed Nov. 25, 2008, the entire content of which is incorporated herein by reference.

The present invention relates to a process for the preparation of water-in-oil and oil-in-water nanoemulsions.

More specifically, the invention relates to a low energy process which allows stable nanoemulsions to be obtained by varying the hydrophilic and lipophilic balance (HLB) of the surface-active agents present in the system.

The nanoemulsion technology, i.e. emulsions whose dimensions are smaller than 500 nm, is a growing technology which transversely affects many industrial areas.

Due to the considerable preparation cost and limited stability during the time, however, nanoemulsions are mainly used today in high value added fields, such as the cosmetic and pharmaceutical field.

In the cosmetic field, for example, nanoemulsions are used for carrying active principles soluble in water into an oil compatible with the skin, in order to bring the active principles directly into the tissues, thus reducing the amount of active principle used. In the pharmaceutical field, on the contrary, nanoemulsions have proved to be effective for spreading anti-bacterial or anti-fungus agents, viruses which are directly transported into the cells by the fusion of the nanoemulsion with the cell membrane.

The potentiality of nanoemulsions for eradicating viruses such as anthrax and AIDS is under study, and also as a carrier of antitumour agents.

There are numerous fields, from the food to the oil industry, in which these products could be used if the cost were lower and if they had a greater stability.

In the food industry, the small dimensions could impart particular organoleptic characteristics to creams and sauces, together with a high stability.

Finally, in the oil industry, water-in-oil nanoemulsions could carry products, not transportable with oil due to their non-solubility, to areas in which large amounts of water cannot be conveyed, due to problems relating to corrosion, damage etc . . .

In particular, nanoemulsions could be used as carriers of scale inhibitors, corrosion inhibitors or wax and asphaltene inhibitors, or for acidic treatment of the formation. They can also be used for cleaning oil pipelines.

Their considerable stability, when suitably prepared, and the fact that the inner water is completely shielded, could make them interesting for carrying additives which are incompatible with each other or for triggering polymerization or gelation reactions in appropriate areas of the well.

At present, the high cost is due to the necessity of using high energy systems, such as high pressure homogenisers, for obtaining them.

The so-called low energy methods are empirical and not easy to implement. In particular, obtaining water-in-oil nanoemulsions is still a problem which is not easy to solve.

Analogously to macroemulsions, for which, however, there is no standard procedure for their preparation but more or less empirical formulation criteria, nanoemulsions also suffer from the lack of scientific criteria for their formulation.

The highest critical point for the formation of nanoemulsions with respect to the corresponding macroemulsions, lies in the higher energy necessary for obtaining them, due to the very small dimensions of the droplets of the dispersed phase (smaller than 500 nm).

The so-called low energy procedures can be carried out through particular areas of the phase diagram, with a very low interface tension, which are areas of either liquid crystals or microemulsions.

It is known, for example, that nanoemulsions can be obtained through a spontaneous emulsioning by means of phase inversion, such as the classical PIT (Phase Inversion Temperature) method [K: Shinoda, H. Saito, J. Colloid Interface Sci. 1 (1949) 311] in particular through certain areas of liquid crystals of the phase diagram [Paqui Izquierdo, Jin Feng, Jordi Esquena, Tharward F. Tadros, Joseph C. Dederen, Mari Josè Garcia, Nùria Azemar, Conxita Solans, Journal of Colloid and Interface Science 285 (2005) 388-394].

In certain cases, oil-in-water nanoemulsions have been obtained by means of phase inversion [Patrick Fernandez, Valeris Andrè, Jens Rieger, Angelika Kuhnle, Colloids and Surfaces A: Physicochem. Eng. Aspects 251 (2004) 53-58] by varying the water/oil ratio (catastrophic inversion, the nanoemulsions obtained are between 100 and 500 nm) or by the dilution of microemulsions [R. Pons, I. Carrera, J. Caelles, J. Rouch, P. Panizza, Advances in Colloid and Interface Science, 106, (2003) 129-146].

It is not so easy to find papers relating to the formation of water-in-oil nanoemulsions through "gently methods" [N. Uson, M. J. Garciaand C. Solans Colloids and Surfaces A: Physicochemical and Engineering Aspect, Volume 250, Issues 1-3, Dec. 10, 2004, pages 415-421; M. Porras, C. Solans, C. Gonzales, A. Martinez, A. Guinart and J. M. Gutierrez Colloids and Surfaces A: Physicochemical and Engineering aspect, Volume 250, Issues 1-3, 10 Dec. 2004, Pages 415-421; M Porras, C. Solans, C. Gonzales,A. Martinez, A. Guinart and J. M. Gitierrez Colloids and Surfaces A: Physicochemical and Engineering Aspects, Volume 249, Issues 1-3, Nov. 30, 2004, pages 115-118; Italian patent application nr. MI 03A002101].

These low energy processes have the disadvantage of being set up case by case, depending on the systems used (type of surface-active agent, water, oil).

Italian patent application nr. MI 03A002101, for example, describes a three-step low energy process for the preparation of water-in-diesel nanoemulsions, comprising the preparation of a blend of surface-active agents so as to obtain a first emulsion, transformation of the first emulsion into a second birefringent emulsion, mixing of the birefringent emulsion with diesel in order to obtain the desired nanoemulsion.

The water-in-gas oil nanoemulsions obtained through this method are practically mono-dispersed, as they comprise a reduced quantities of a composition of non-ionic surface-active agents (1 to 5% by weight; much lower than that of microemulsions) and are characterized by a high stability.

A low energy process has now been found for the preparation of mono-dispersed water-in-oil and oil-in-water nanoemulsions, with a high stability, having the characteristic of being simpler and with a wider applicability range with respect to those described in the known art.

The process of the invention also allows the preparation of nanoemulsions with a high formation kinetics, so that they are obtained within a few hours after their dilution, whereas the method described in patent application nr. MI 03A002101 requires longer times (a few days) for their formation.

The process of the invention is based on the capacity of a system based on water and oil, of inverting the phase by varying the hydrophilic/lipophilic balancing of the surface active agents present in the system (HLB).

The inversion takes place by the dilution of a homogeneous blend (concentrated precursor) characterized by a certain HLB and an interface tension lower than 1 mN/m, in a dispersing phase (oil or water) which contains a surface-active agent capable of conferring a different HLB to the final dispersion with respect to the precursor.

It has also been found that the selection of the final HLB of the nano-emulsion can be effected on the basis of the HLB of the corresponding micro-emulsion. This micro-emulsion can be easily obtained without any particular procedures, but: simply by using a higher quantity of surface-active agent.

The HLB of the nanoemulsion is lower than that of the precursor in the case of water-in-oil dispersions, whereas it is higher than that of the precursor, in the case of oil-in-water dispersions. During dilution, an instantaneous phase inversion occurs, together with the formation of the nanoemulsion.

In accordance with the above, a process for the preparation of a water-in-oil or oil-in-water nanoemulsion in which the dispersed phase is distributed in the dispersing phase, in the form of droplets having a diameter ranging from 1 to 500 nm, represents a first object of the present invention, which comprises:
1) the preparation of a homogeneous water/oil blend (1) characterized by an interface tension lower than 1 mN/m, comprising water in a quantity of 30 to 70% by weight, at least two surface-active agents having a different HLB, selected from non-ionic, anionic, polymeric surface-active agents, the latter being present in such a quantity as to make the blend homogeneous;
2) the dilution of the blend (1) in a dispersing phase consisting of oil or water with the addition of a surface-active agent selected from non-ionic, anionic polymeric surface-active agents, the quantity of the dispersing phase and surface-active agent being such as to obtain a nanoemulsion having a HLB different from that of the blend (1).

The HLB of the final nanoemulsion is selected on the basis of that of the corresponding micro-emulsion characterized by the same water/oil ratio as the nanoemulsion, but with a total quantity of surface-active agents such as to make the blend homogeneous by the simple addition of all the components.

In particular, when water-in-oil emulsions are to be obtained, an amount of dispersing phase and surface-active agent is used in order to obtain a nanoemulsion having a HLB higher than that of the blend (1).

Nano-emulsions are obtained only by operating in accordance with the process of the invention: the preparation of a blend having the same final composition, but without following the procedure specified (preparation of the precursor, order of addition of the reagents, etc . . . ) does not produce a limpid nanoemulsion, but an opaque and milky macro-emulsion characterized by droplets having dimensions well above a micron.

Homogeneous blends can be advantageously prepared, comprising from 5 to 50% by weight of surface-active agents and in which the weight ratio of the surface-active agents used gives a HLB value higher than 8, preferably between 10 and 15 for non-ionic, and over 20 for anionic surface-active agents.

The concentration of surface-active agents in the blend is in relation to the final water/oil amount which is to be dispersed. The weight proportion between the concentration of the surface-active agents in the blend and the amount of water/oil to be dispersed, can vary from 0.07 to 3.5, preferably from 0.1 to 2.

The surface-active agents used for the preparation of the blend can be selected from non-ionic, anionic, polymeric surface-active agents, preferably non-ionic and polymeric surface-active agents.

Blends can be suitably prepared comprising a first surface-active agent selected from non-ionic lipophilic surface-active agents (A type), a second surface-active agent selected from non-ionic hydrophilic surface-active agents (B type), a third surface-active agent selected from polymeric surface-active agents (C type), the composition of surface-active agents (A)+(B)+(C) having a HLB ranging from 8 to 16, preferably from 10 to 15.

Preferred formulations include a lipophilic non-ionic surface-active agent of the fatty acid ester group having a HLB higher than 11 and a non-ionic, polymeric surface-active agent with a HLB varying from 4 to 14.

The mix has the appearance of a limpid to translucent solution and is characterized by a high stability as it allows nanoemulsions to be prepared by dilution even up to a year after its preparation. The blend maintains its properties even after being subjected to freezing.

The preparation can be effected at a temperature ranging from 5 to 60° C.

In practice, in order to prepare the homogeneous precursor blends of nano-emulsions, the mixture of surface-active agents, selected from non-ionic, anionic and polymeric surface-active agents, is dissolved in oil so as to obtain the desired HLB, and when the dissolution is complete, the water solution is added under stirring.

The aqueous solution can be deionised water or water with additives. At the end of the addition, the blend will appear homogeneous and limpid. This precursor blend can be used for preparing water-in-oil and oil-in-water nanoemulsions.

In order to formulate water-in-oil nanoemulsions, the precursor mix is added, at room temperature, slowly, and under stirring to a solution consisting of oil and the lipophilic surface-active agent selected from non-ionic and polymeric surface-active agents.

In order to formulate oil-in-water nanoemulsions, the precursor mix is added, at room temperature, slowly, and under stirring to a solution consisting of an aqueous solution and the hydrophilic surface-active agent selected from non-ionic and polymeric surface-active agents.

Normally, the nanoemulsion preparation is effected at a temperature ranging from 5 to 60° C.

The complete transformation into the final nano-emulsion is revealed by the limpid/translucent appearance and by the monomodal distribution of the dispersed phase droplets.

The nanoemulsions obtained through the process of the invention can be formulated with a different content of dispersed water or oil, they are stable for over 6 months, do not require particular care for their preservation, and maintain their characteristics up to a temperature of 70° C.

It is normally possible to prepare nanoemulsions having a wider concentration range of dispersed phase, by means of a sole formulation of a homogeneous blend (or precursor).

When water-in-oil emulsions are to be obtained, the dilution is effected using an amount of dispersing phase and surface-active agent such as to obtain a nanoemulsion having a HLB at least 0.5 units lower with respect to that of the homogeneous blend (1).

When the surface-active agent, which is dissolved in the oily phase, is selected from non-ionic lipophilic surface-active agents, preferably non-ionic surface-active agents of the group of esters of fatty acids, and the homogeneous blend is prepared with non-ionic and polymeric surface-active agents, the nanoemulsion must have a HLB 0.8-5 units lower.

When oil-in-water emulsions are to be obtained, the dilution is effected with a quantity of dispersing phase and surface-active agent such as to obtain a nanoemulsion having a HLB at least 0.5 units higher with respect to that of the homogeneous blend (1). When the surface-active agent which is dissolved in the aqueous phase is selected from non-ionic hydrophilic surface-active agents, preferably from non-ionic surface-active agents of the group of alkyl glucosides and the homogeneous blend is prepared with non-ionic and polymeric surface-active agents, the nano-emulsion should have a HLB 0.8-5 units higher.

Water-in-oil nanoemulsions can be prepared by operating according to the procedure of the invention, having a HLB value ranging from 6 to 14, comprising a water content ranging from 1 to 30%, and a total amount of surface-active agents ranging from 0.1 to 20%, the complement to a hundred being oil.

Water-in-oil nanoemulsions can preferably be prepared with a HLB value ranging from 9 to 13, comprising a water content ranging from 5 to 25% and total surface-active agents ranging from 1.5 to 12%, the complement to a hundred being oil.

Oil-in-water nanoemulsions can also be conveniently prepared having a HLB value higher than 10, comprising an oil content ranging from 1% to 30% and total surface-active agents from 0.1 to 20%, the complement to a hundred being oil.

Oil-in-water nanoemulsions can be preferably prepared with a HLB value ranging from 11 to 16, comprising an oil content ranging from 5 to 25% and total surface-active agents from 1.5 to 12%, the complement to a hundred being water.

Any polar or apolar oil, preferably insoluble in water, can be used for the purposes of the present invention.

The oil is preferably selected from the group of linear or branched hydrocarbons, such as, for example, dodecane, or complex mixtures of hydrocarbons such as gas oil, kerosene, soltrol, mineral spirits.

As far as the water which can be used for the preparation of the nanoemulsions of the present invention is concerned, this can be of any origin.

In the case of applications in the oil industry, it is preferable, for obvious economical reasons, for the water to be available close to the nanoemulsion preparation site of the present invention.

Different types of water can be used, such as demineralized water, saltwater, water with additives.

In principle, any additive can be englobed in the nano-emulsions and they can be used in the food, oil, cosmetic, pharmaceutical and fuel industries, where they are used as additive carriers.

In particular the nanoemulsions of the present invention can be suitably used in the oil industry, for the injection of additives into the well, which cannot be carried with the oil (as they are not soluble) or for the injection of acid solutions in areas which cannot be reached by large amounts of water due to problems relating to corrosion, damage, etc . . .

The nanoemulsions of the invention can also be formulated so as to contemporaneously carry two different additives, incompatible with each other, such as, for example, a scale inhibitor in aqueous phase (dispersed phase) and a wax/asphaltene inhibitor in organic phase (the two additives are incompatible as they are soluble in different solvents), or a scale inhibitor in aqueous phase and a corrosion inhibitor in organic phase (the two additives are chemically incompatible). Finally, they can be used for the cleaning of oil pipelines.

When used upstream, the nanoemulsions must not damage the formation and, under suitable conditions, release the dispersed phase containing the additives.

The nanoemulsions can also be formulated using aqueous solutions as dispersed phase. These aqueous solutions can consist of salt solutions, such as, for example, chlorides, bromides, sulphates, phosphates of alkaline metals (sodium, potassium), alkaline-earth metals (calcium) or transition metals (silver, cobalt, nickel, copper, zinc, iron).

The aqueous solutions can also consist of hydro-soluble additive solutions, such as, for example, urea, oxygenated water, scale inhibitors (such as, for example, phosphono-carboxylic acids, amino phosphonic acids, organic sulphates, etc . . . ).

The aqueous solutions can contain from 0.1 to 50% by weight of additive and preferably from 5 to 20%.

In particular, when scale inhibitors are used, these are normally present at concentrations ranging from 5 to 15%.

Nanoemulsions containing water with additives are normally prepared by diluting a precursor already containing the desired additive solution in the oily dispersing phase containing the lipophilic surface-active agent.

The following examples are provided for a better understanding of the present invention.

EXAMPLES

In the following examples, the procedures are described for preparing water-in-oil nanoemulsions with increasing quantities of dispersed water.

Example 1

Formulation of the precursor.

The precursor suitable for the formulation of water-in-oil nanoemulsions, in which the oil is dodecane and the dispersed phase is deionised water, can be formulated according to the following procedure.

0.177 g of Atlox 4914 (Uniqema), 1.563 gr of Span 80 (Fluka) and 3.588 gr. of Glucopone 600 CS UP (Fluka, 50% water solution) are weighed in a single container and dissolved in 8.233 gr. of dodecane. When the dissolution is complete, 6.439 gr. of deionised water are added under vigorous stirring by means of a magnetic stirrer. The precursor is characterized by a HLB value of 10.8 and is indefinitely stable.

Example 2

Formulation of nanoemulsions with 6.8% of water as dispersed phase.

0.073 gr of Span 80 are dissolved in 8.275 gr of dodecane in order to obtain 10 gr of nanoemulsion. 1.652 gr of precursor, as prepared in example 1, are slowly added under stirring (magnetic stirrer) to this solution. The emulsion obtained has a transparent-translucent appearance, it is characterized by a HLB value of 9.6 and has the following composition:
    total surface-active agents=3.65% by weight
    dodecane=89.55% by weight
    water=6.8% by weight The nanoemulsion thus formulated has droplets of dispersed phase around 30-40 nm, a polydispersity index lower than 0.1 and it is stable for over a year.

Example 3

Formulation of nanoemulsions with 10% of water as dispersed phase.

0.096 gr of Span 80 are dissolved in 7.475 gr of dodecane in order to obtain 10 gr of nanoemulsion. 2.429 gr of precursor, as prepared in example 1, are slowly added under stirring (magnetic stirrer) to this solution. The emulsion obtained has a transparent-translucent appearance, it is characterized by a HLB value of 9.7 and has the following composition:
- total surface-active agents=5.25% by weight
- dodecane=84.75% by weight
- water=10% by weight The nanoemulsion thus formulated has droplets of dispersed phase around 30-50 nm, a polydispersity index lower than 0.15 and is stable for over a year.

Example 4

Formulation of nanoemulsions with 20% of water as dispersed phase.

0.131 gr of Span 80 are dissolved in 5.010 gr of dodecane in order to obtain 10 gr of nanoemulsion. 4.858 gr of precursor, as prepared in example 1, are slowly added under stirring (magnetic stirrer) to this solution. The emulsion obtained has a transparent-translucent appearance, it is characterized by a HLB value of 10 and has the following composition:
- total surface-active agents=9.9% by weight
- dodecane=70.1% by weight
- water=20% by weight The nanoemulsion thus formulated has droplets of dispersed phase around 40-60 nm, a polydispersity index lower than 0.2 and it is stable for over six months.

In the following series of examples the procedures are described for preparing water-in-oil nanoemulsions containing additive solutions as dispersed phase, with different concentrations of additives and dispersed phase.

Example 5

Preparation of a precursor containing a 5% by weight solution of a hydrosoluble additive.

The precursor suitable for the formulation of water-in-oil nanoemulsions, in which the oil is dodecane and the dispersed phase is an aqueous solution containing 5% by weight of a scale inhibitor, can be formulated according to the following procedure.

0.151 gr of Atlox 4914 (Unigema), 1.191 gr of Span 80 (Fluka) and 3.342 gr of Glucopone 600 CS UP (Fluka, 50% solution in water) are weighed in a single container and are dissolved in 8.153 gr of dodecane. When the dissolution is complete, 6.823 gr of a 5% by weight aqueous solution of an scale inhibitor (for example a phosphino-polycarboxylic acid or a sodium phosphono-carboxylate) are added under vigorous stirring on a magnetic stirrer. The blend thus obtained is characterized by a HLB value of 11.35 and is indefinitely stable.

Example 6

Preparation of a precursor containing a 10% weight solution of a hydrosoluble additive.

The precursor suitable for the formulation of water-in-oil nanoemulsions, in which the oil is dodecane and the dispersed phase is an aqueous solution containing 10% by weight of an scale inhibitor, can be formulated according to the following procedure.

0.151 gr of Atlox 4914 (Unigema), 1.023 gr of Span 80 (Fluka) and 3.676 gr of Glucopone 600 CS UP (Fluka, 50% solution in water) are weighed in a single container and are dissolved in 7.828 gr of dodecane. When the dissolution is complete, 6.656 gr of a 10% weight aqueous solution of an scale inhibitor (for example a phosphino-polycarboxylic acid or a sodium phosphono-carboxylate) are added under vigorous stirring on a magnetic stirrer. The blend thus obtained is characterized by a HLB value of 12 and is indefinitely stable.

Example 7

Preparation of a precursor containing a 15% weight solution of a hydrosoluble additive.

The precursor suitable for the formulation of water-in-oil nanoemulsions, in which the oil is dodecane and the dispersed phase is an aqueous solution containing 15% by weight of a scale inhibitor, can be formulated according to the following procedure.

0.151 gr of Atlox 4914 (Unigema), 0.869 gr of Span 80 (Fluka) and 3.985 gr of Glucopone 600 CS UP (Fluka, 50% solution in water) are weighed in a single container and are dissolved in 7.519 gr of dodecane. When the dissolution is complete, 6.501 gr of a 15% by weight aqueous solution of a scale inhibitor (for example a phosphino-polycarboxylic acid or a sodium phosphono-carboxylate) are added under vigorous stirring on a magnetic stirrer. The blend thus obtained is characterized by a HLB value of 12.60 and is indefinitely stable.

Example 8

Formulation of nanoemulsions with the addition in aqueous phase of scale inhibitors.

0.081 gr. of Span 80 are dissolved in 3.094 gr of dodecane, in order to obtain 10 gr of nanoemulsion. 2.826 gr of precursor, as prepared in example 5, are added to this solution, slowly and under stirring (magnetic stirrer). The emulsion obtained has a transparent-translucent appearance, it is characterized by a HLB value of 10.30 and has the following composition:
- total surface-active agents=8.57% by weight
- dodecane=71.09% by weight
- water=19.53% by weight
- additive=0.83% by weight The nanoemulsion thus formulated has droplets of dispersed phase around 40-60 nm, a polydispersity index lower than 0.2 and it is stable for over six months.

Example 9

Formulation of nanoemulsions with the addition in aqueous phase of scale inhibitors.

0.074 gr. of Span 80 are dissolved in 8.3 gr of dodecane, in order to obtain 10 gr of nanoemulsion. 1.6 gr of precursor, as prepared in example 6, are added to this solution, slowly and under stirring (magnetic stirrer). The emulsion obtained has a transparent-translucent appearance, it is characterized by a HLB value of 10.35 and has the following composition:
- total surface-active agents=3.25% by weight
- dodecane=89.71 by weight water=6.5% by weight
additive=0.55% by weight The nanoemulsion thus formulated has droplets of dispersed phase around 40-60 nm, a polydispersity index lower than 0.2 and it is stable for over six months.

Example 10

Formulation of nanoemulsions with the addition in aqueous phase of scale inhibitors.

0.101 gr. of Span 80 are dissolved in 7.5 gr of dodecane, in order to obtain 10 gr of nanoemulsion. 2.4 gr of precursor, as prepared in example 6, are added to this solution, slowly and under stirring (magnetic stirrer). The emulsion obtained has a transparent-translucent appearance, it is characterized by a HLB value of 10.45 and has the following composition:
total surface-active agents=4.75% by weight
dodecane=84.71% by weight
water=9.72% by weight
additive=0.83% by weight The nanoemulsion thus formulated has droplets of dispersed phase around 40-60 nm, a polydispersity index lower than 0.2 and it is stable for over six months.

Example 11

Formulation of nanoemulsions with the addition in aqueous phase of scale inhibitors.

0.134 gr. of Span 80 are dissolved in 6.3 gr of dodecane, in order to obtain 10 gr of nanoemulsion. 3.5 gr of precursor, as prepared in example 6, are added to this solution, slowly and under stirring (magnetic stirrer). The emulsion obtained has a transparent-translucent appearance, it is characterized by a HLB value of 10.6 and has the following composition:
total surface-active agents=6.84% by weight
dodecane=77.68% by weight
water=14.27% by weight
additive=1.21% by weight The nanoemulsion thus formulated has droplets of dispersed phase around 40-60 nm, a polydispersity index lower than 0.2 and it is stable for over six months.

Example 12

Formulation of nanoemulsions with the addition in aqueous phase of scale inhibitors.

0.157 gr. of Span 80 are dissolved in 5.134 gr of dodecane, in order to obtain 10 gr of nanoemulsion. 4.709 gr of precursor, as prepared in example 6, are added to this solution, slowly and under stirring (magnetic stirrer). The emulsion obtained has a transparent-translucent appearance, it is characterized by a HLB value of 10.7 and has the following composition:
total surface-active agents=8.91% by weight
dodecane=70.41% by weight
water=19.07% by weight
additive=1.62% by weight The nanoemulsion thus formulated has droplets of dispersed phase around 40-60 nm, a polydispersity index lower than 0.2 and it is stable for over six months.

Example 13

Formulation of nanoemulsions with the addition in aqueous phase of scale inhibitors.

0.070 gr. of Span 80 are dissolved in 3.105 gr of dodecane, in order to obtain 10 gr of nanoemulsion. 2.826 gr of precursor, as prepared in example 7, are added to this solution, slowly and under stirring (magnetic stirrer). The emulsion obtained has a transparent-translucent appearance, is characterized by a HLB value of 11.54 and has the following composition:
total surface-active agents=8.62% by weight
dodecane=70.35% by weight
water=18.61% by weight
additive=2.41% by weight The nanoemulsion thus formulated has droplets of dispersed phase around 40-60 nm, a polydispersity index lower than 0.2 and it is stable for over six months.

In the following series of examples the procedures are described for preparing water-in-oil nanoemulsions with different types of oil as continuous phase.

Example 14

Formulation of nanoemulsions with the addition in aqueous phase of scale inhibitors, using gas oil, or soltrol or mineral spirits as continuous phase.

Nanoemulsions can be obtained by indifferently using one of the above-mentioned hydrocarbons by applying the following procedure.

0.085 gr. of Span 80 are dissolved in 3.090 gr of diesel or soltrol or mineral spirits to obtain 6 gr of nanoemulsion. 2.826 gr of precursor, prepared with the same procedure described in example 6, but using gas oil or soltrol or mineral spirits as organic phase, are added to this solution, slowly and under stirring (magnetic stirrer). The emulsion obtained has a transparent-translucent appearance, it is characterized by a HLB value of 10.8 and has the following composition:
total surface-active agents=8.7% by weight
hydrocarbon=70.6% by weight
water=19.1% by weight
scale inhibitor=1.6% by weight The nanoemulsion thus formulated has droplets of dispersed phase around 40-60 nm, a polydispersity index lower than 0.2 and it is stable for over six months.

Example 15

Formulation of nanoemulsions with the addition in aqueous phase of scale inhibitors, using kerosene as continuous phase.

0.068 gr. of Span 80 are dissolved in 3.106 gr of kerosene to obtain 6 gr of nanoemulsion. 2.826 gr of precursor, prepared with the same procedure described in example 6, but using kerosene as organic phase, are added to this solution, slowly and under stirring (magnetic stirrer). The emulsion obtained has a transparent-translucent appearance, it is characterized by a HLB value of 11.0 and has the following composition:
total surface-active agents=8.5% by weight
hydrocarbon=70.8% by weight
water=19.1% by weight
scale inhibitor=1.6% by weight The nanoemulsion thus formulated has droplets of dispersed phase around 40-60 nm, a polydispersity index lower than 0.2 and it is stable for over six months.

In the following series of examples the procedures are described for preparing water-in-oil nanoemulsions with the addition of additives in both the continuous and dispersed phase.

Example 16

Preparation of the precursor with the addition in aqueous phase of scale inhibitors and in the organic phase of wax/asphaltene inhibitors.

The precursor suitable for the formulation of water-in-oil nanoemulsions, in which oil is a 10% solution by weight of a wax/asphaltene inhibitor (FX 1972 of Ondeo Nalco) in dodecane and the dispersed phase is an aqueous solution containing 10% by weight of a scale inhibitor, can be formulated according to the following procedure.

0.151 gr of Atlox 4914 (Uniqema), 0.946 gr of Span 80 (Fluka) and 3.831 gr of Glucopone 600 CS UP (Fluka 50% water solution) are weighed in a single container and are dissolved in 7.836 gr. of a solution of wax/asphaltene inhibitor in dodecane. When the dissolution is complete, 6.579 gr. of a 10% by weight water solution of a scale inhibitor (for example polycarboxylic phosphine acid or a sodium phosphono-carboxylate) are added under vigorous stirring on a magnetic stirrer. The blend thus obtained, characterized by a HLB value of 12.30 is indefinitely stable.

Example 17

Formulation of nanoemulsions with the addition in aqueous phase of scale inhibitors and in the organic phase with wax/asphaltene inhibitors.

0.097 gr of Span 80 are dissolved in 2.549 gr of a 10% by weight solution of wax/asphaltene inhibitor in dodecane in order to obtain 5 gr of nanoemulsion. 2.355 gr of a precursor, as prepared in example 16, are slowly added under stirring (magnetic stirrer) to this solution. The emulsion obtained has a transparent-translucid appearance, it is characterized by a HLB value of 10.75 and has the following composition:
- total surface-active agents=9.4% by weight
- dodecane=62.6% by weight
- water=19.5% by weight
- additive in aqueous phase (scale inhibitor)=1.6% by weight
- additive in organic phase (wax inhibitor)=6.9% by weight.

The nanoemulsion thus formulated has droplets of dispersed phase around 30-40 nm, a polydispersity index lower than 0.2 and it is stable for over six months.

Example 18

Formulation of nanoemulsions with the addition in aqueous phase of scale inhibitors and in the organic phase with corrosion inhibitors.

0.157 gr of Span 80 are dissolved in 5.134 gr of a solution containing 1300 ppm of a corrosion inhibitor (Inicor R200 of Lamberti) in dodecane in order to obtain 10 gr of nanoemulsion. 4.709 gr of a precursor prepared by using additive-free dodecane as organic phase and, as aqueous phase, a 10% solution of a scale inhibitor, as described in example 6, are slowly added under stirring (magnetic stirrer) to this solution. The emulsion obtained has a transparent-translucid appearance, it is characterized by a HLB value of 10.70 and has the following composition:
- total surface-active agents=8.9% by weight
- dodecane=70.4% by weight
- water=19.1% by weight
- additive in aqueous phase (scale inhibitor)=1.6% by weight
- additive in organic phase (corrosion inhibitor)=700 ppm.

The nanoemulsion thus formulated has droplets of dispersed phase around 3040 nm, a polydispersity index lower than 0.2 and it is stable for over six months.

In the following series of examples the procedures are described for preparing oil-in-water emulsions.

Example 19

Formulation of the precursor for oil-in-water nanoemulsions.

The precursor suitable for the formulation of oil-in-water nanoemulsions, in which the oil is dodecane and the dispersed phase is deionised water, can be formulated according to the following procedure.

0.177 g of Atlox 4913 (Uniqema), 1.284 gr of Span 80 (Fluka) and 4.147 gr. of Glucopone 600 CS UP (Fluka, 50% water solution) are weighed in a single container and are dissolved in 8.233 gr. of dodecane. When the dissolution is complete, 6.160 gr. of deionised water are added under vigorous stirring by means of a magnetic stirrer. The precursor is characterized by a HLB value of 12 and is indefinitely stable.

Example 20

Formulation of oil-in-water nanoemulsions with 6.8% of dodecane as dispersed phase.

0.174 gr of Span 80 are dissolved in 4.8 gr of water. 1.0 gr of a precursor as prepared in example 19, are slowly added under stirring (magnetic stirrer) to this solution. The emulsion obtained has a transparent-translucent appearance, it is characterized by a HLB value of 13.5 and has the following composition:
- total surface-active agents=4.4% by weight
- dodecane=6.8% by weight
- water=88.8% by weight The nanoemulsion thus formulated has droplets of dispersed phase around 30-40 nm, a polydispersity index lower than 0.2 and it is stable for over six months.

Some comparative examples are provided hereunder which demonstrate that nanoemulsions are not obtained if the procedures claimed in this patent are not followed.

Example 21 (Comparative)

Mixing of the ingredients of the nanoemulsion corresponding to example 4 (20% aqueous phase) without following the procedure indicated in the patent.

0.043 gr of Atlox 4914 (Uniqema), 0.51 gr of Span 80 (Fluka) and 0.88 gr of Glucopone 600 CS UP (Fluka, 50% water solution) are dissolved in 7 gr of dodecane and 1.57 gr of water are added. A suspension is obtained having the same composition as the nanoemulsion of example 4 and the same HLB=10, but the appearance is opaque and milky and the dispersed phase has droplets having dimensions of over 1 micron.

Composition of the suspension:
- total surface-active agents=9.9%
- dodecane=70.1%
- water=20%

Example 22 (Comparative)

Preparation of a nanoemulsion having a non-optimal final HLB.

The precursor blend having a HLB of 10.8 is prepared as in example 1. The water-in-oil nanoemulsion containing 20% of dispersed phase is formulated however so as to be characterised by a HLB of 9.6 instead of HLB=10, as indicated in example 4. 0.214 gr of Span 80 (Fluka) are dissolved in 4.928 gr of dodecane. 4,858 gr of a precursor blend prepared as in example 1 are slowly added under stirring to the solution thus obtained. A suspension is obtained characterised by a HLB of 9.6 but having an opaque and milky appearance, with the dimensions of the dispersed phase droplets higher than 500 nm.
Suspension composition:
total surface-active agents=10.7%
dodecane=69.3%
water=20%

Example 23 (Comparative)

Preparation of a nanoemulsion by the dilution of a non-homogeneous precursor blend 0.177 gr of Atlox 4914 (Uniqema), 1.744 gr of Span 80 (Fluka) and 3.226 gr. of Glucopone 600 CS UP (Fluka, 50% water solution) are weighed in a single container and are dissolved in 8.233 gr. of dodecane in order to prepare the precursor blend. When the dissolution is complete, 6.620 gr. of deionised water are added under vigorous stirring by means of a magnetic stirrer. The precursor is characterized by a HLB value of 10.2 and is separated into two phases. 0.033 of Span 80 (Fluka) are dissolved in 5.100 gr of dodecane. 4.900 gr of a precursor mix prepared as described in this example, are slowly added, under stirring to the solution thus obtained.

A suspension is obtained, characterised by a HLB of 10, but having an opaque and milky appearance, with the tendency of depositing into two phases.
Suspension composition:
total surface-active agents=9%
dodecane=71%
water=20%.

Example 24

Example of the preparation of a micro-emulsion with the aim of defining the HLB suitable for the formulation of the nanoemulsion.

In order to obtain a homogeneous micro-emulsion with a HLB of 9.6, containing 7% of aqueous phase, a concentration of surface-active agent of at least 7% is necessary. In particular, 0.763 gr of Span 80 (Fluka), 1.134 gr of Glucopone CS UP (Fluka 50% water solution) and 0.070 gr of Atlox 4914 (Uniqema) are dissolved in 17.2 gr of dodecane and 0.81 gr of water are added, under stirring until a homogeneous product is obtained. A limpid micro-emulsion is thus obtained having a HLB of 9.6 with a composition equal to:
total surface-active agents=7%
water=7%
dodecane=86%
Nanoemulsion applications upstream:

Example 25

Behaviour to temperature:
Nanoemulsions prepared according to the procedure described in example 6, with a weight composition equal to 70.4% of dodecane, 19.1% of water, 8.9% of surface-active agents and 1.6% of scale inhibitor of the group of phosphono-succinic succinic acids, are charged into an autoclave at a pressure of 30 bars and maintained at temperatures of 60° C., 80° C., 100° C. for 8 hours.

The nanoemulsion remains unaltered up to a temperature of 80° C., when it begins to show a slight separation of the aqueous phase. At a temperature of 100° C., the aqueous phase is completely separated, allowing the release of the hydrosoluble additive, which follows the same destiny as the aqueous phase.

Example 26

Behaviour to flushing on a porous medium:
A column having a height of 20 cm and a diameter of 1.9 cm is packed with quartzite having a particle-size greater than 230 mesh and flushed with dodecane at a temperature of 90° C. The initial permeability to dodecane proves to be 55 mD, with a pore volume (PV) equal to 28.9 cm$^3$.

180 ml (equal to 6.2 PV) of a nanoemulsion prepared according to the procedure described in example 6, with a composition by weight equal to 70.4% of dodecane, 19.1% of water, 8.9% of surface-active agents and 1.6% of a scale inhibitor of the group of phosphono-succinic acids is flushed in the quartzite column at a flow-rate of 120 mg/h and a temperature of 90° C., maintaining an overpressure of 2.8 bars. Under these conditions, the nanoemulsion separates the aqueous phase containing the scale inhibitor, allowing it to be released and deposited on the quartzite.

At the end, the column is flushed again with dodecane until the complete separation of the nanoemulsion, and the permeability to dodecane is determined again.

During the flushing of the nanoemulsion, the pressure differential ($\Delta p$) undergoes a slight increase, passing from 1.9 to 3.1, due to the greater viscosity of the emulsion with respect to the dodecane, the final permeability to dodecane, however, is not modified with respect to its initial value, confirming that the nanoemulsion is filterable and non-damaging.

At the end of the test, the quartzite contained in the column is discharged and analyzed to evaluate the adsorption of the inhibitor, which proves to be equal to 0.6 mg/g quartzite (4% with respect to the total), typical of scale inhibitors of this group (REF: M. Andrei, A. Malandrino, Petrol. Sci Technol., 2003, 21 (7-8)1295-1315).

The invention claimed is:

1. A low energy process for the preparation of an oil-in-water nanoemulsion wherein a dispersed phase is distributed in a dispersing phase in the form of droplets having a diameter ranging from 1 to 500 nm, said process consisting of:
diluting a
homogeneous water/oil blend (I) having an interface tension lower than 1 mN/m and comprising water in an amount of 30 to 70% by weight and at least two surface-active agents having a different HLB, said surface-active agents being selected from the group consisting of non-ionic surface-active agents, anionic surface-active agents, and polymeric surface-active agents, and said surface-active agents being present in said water/oil blend (I) an amount of from 5 to 50% by weight
in a
dispersing phase consisting of water and a surface-active agent selected from the group consisting of a non-ionic surface-active agent, an anionic surface-active agent, and a polymeric surface-active agent, the quantity of the dispersing phase and the surface-active agent being sufficient to obtain an oil-in-water nanoemulsion having an HLB higher than that of said homogeneous water/oil blend (I), wherein during dilution a spontaneous and instantaneous phase inversion occurs, together with the formation of the nanoemulsion.

2. The process according to claim 1, wherein, in the homogeneous blend (I), the weight ratio between the surface-active agents produces a HLB value higher than 8.

3. The process according to claim 2, wherein the surface-active agents are selected from non-ionic surface-active agents and the weight ratio between the surface-active agents produces a HLB ranging from 10 to 15.

4. The process according to claim 2, wherein the surface-active agents are selected from anionic surface-active agents and the weight ratio between the surface-active agents produces a HLB higher than 20.

5. The process according to claim 2, wherein the weight proportion between the concentration of surface-active agents in the blend and the quantity of water/oil to be dispersed varies from 0.07 to 3.5.

6. The process according to claim 5, wherein the weight proportion between the concentration of surface-active agents in the blend and the quantity of water/oil to be dispersed varies from 0.1 to 2.

7. The process according to claim 1, wherein the surface-active agents having a different HLB are selected from non-ionic and polymeric surface-active agents.

8. The process according to claim 1, wherein the surface-active agents having a different HLB are selected from the group consisting of a first surface-active agent selected from non-ionic lipophilic surface-active agents (type A), a second surface-active agent selected from non-ionic hydrophilic surface-active agents (type B), and a third surface-active agent selected from polymeric surface-active agents (type C), the composition of surface-active agents (A)+(B)+(C) having a HLB ranging from 8 to 16.

9. The process according to claim 8, wherein the composition of surface-active agents (A)+(B)+(C) has a HLB ranging from 10 to 15.

10. The process according to claim 1, wherein the surface-active agents having a different HLB consist of a non-ionic lipophilic surface-active agent of the group of esters of fatty acids with a HLB lower than 11, a non-ionic hydrophilic surface-active agent of the group of alkyl glucosides with a HLB higher than 11 and a non-ionic polymeric surface-active agent with a HLB varying from 4 to 14.

11. The process according to claim 1, wherein the oil-in-water nanoemulsion is prepared by dissolving a hydrophilic surface-active agent in water and slowly adding the homogeneous blend (I) under stirring, said hydrophilic surface-active agent being selected from the group consisting of non-ionic surface-active agents and polymeric surface-active agents.

12. The process according to claim 1, wherein the diluting of the blend (I) is performed at a temperature ranging from 5° C. to 60° C.

13. The process according to claim 1, wherein the quantity of dispersing phase and the surface-active agent is sufficient to obtain a nanoemulsion having an HLB 0.5 units higher with respect to that of homogeneous water/oil blend (I).

14. The process according to claim 13, wherein:
homogeneous water/oil blend (I) comprises non-ionic and polymeric surface-active agents,
the dispersing phase consists of water and a non-ionic surface-active agent selected from the group consisting of alkyl glucosides, and
the quantity of dispersing phase and surface-active agent is sufficient to obtain a nanoemulsion having a HLB at least 0.8-5 units higher than homogeneous water/oil blend (I).

15. The process according to claim 1, wherein the oil for the preparation of the oil-in-water nanoemulsion is selected from the group consisting of linear hydrocarbons, branched hydrocarbons, and complex hydrocarbon blends.

16. The process according to claim 15. wherein the oil is selected from the group consisting of dodecane, diesel, kerosene, soltrol, and mineral spirits.

17. The process according to claim 1, wherein the water for the preparation of the oil-in-water nanoemulsion is selected from the group consisting of demineralised water, saltwater, and water containing additives.

* * * * *